US012082897B2

United States Patent
Lin et al.

(10) Patent No.: US 12,082,897 B2
(45) Date of Patent: *Sep. 10, 2024

(54) SYSTEMS AND METHODS FOR CONSTRAINING A FIELD OF VIEW IN A VIRTUAL REALITY SURGICAL SYSTEM

(71) Applicant: INTUITIVE SURGICAL OPERATIONS, INC., Sunnyvale, CA (US)

(72) Inventors: Henry C. Lin, San Jose, CA (US); May Quo-Mei Liu, Hillsborough, NC (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,843

(22) Filed: Jan. 24, 2023

(65) Prior Publication Data
US 2023/0157776 A1    May 25, 2023

Related U.S. Application Data

(63) Continuation of application No. 16/496,153, filed as application No. PCT/US2018/028376 on Apr. 19, 2018, now Pat. No. 11,589,937.

(Continued)

(51) Int. Cl.
*A61B 34/35* (2016.01)
*A61B 34/10* (2016.01)
(Continued)

(52) U.S. Cl.
CPC .............. *A61B 34/35* (2016.02); *A61B 34/10* (2016.02); *A61B 90/37* (2016.02); *A61B 90/50* (2016.02);
(Continued)

(58) Field of Classification Search
CPC ......... A61B 34/35; A61B 34/10; A61B 90/37; A61B 90/50; A61B 34/25;
(Continued)

(56) References Cited

U.S. PATENT DOCUMENTS 6,126,450 A    10/2000  Mukai et al.
10,510,267 B2  12/2019  Jarc et al.
(Continued)

FOREIGN PATENT DOCUMENTS

EP    2856923 A1   4/2015
EP    2939589 A1   11/2015
(Continued)

OTHER PUBLICATIONS

Edmondson, Matthew J., et al. "Looking towards objective quality evaluation in colonoscopy: analysis of visual gaze patterns." Journal of Gastroenterology and Hepatology 31.3 (2016): 604-609. (Year: 2016).*

(Continued)

*Primary Examiner* — Maurice L. McDowell, Jr.
(74) *Attorney, Agent, or Firm* — Haynes & Boone, LLP (57) ABSTRACT

A method of operating a surgical control system comprises generating an image of a surgical environment from a viewpoint of an imaging tool. The image includes a field of view. The method further comprises displaying the image on a display system configured to be mounted to a head of a user. The method further comprises detecting a movement of the head of the user and determining if the movement of the user's head is within a boundary corresponding to the field of view. The method further comprises, if the movement of the user's head is determined to be within the boundary: generating a changed image of the surgical environment from a changed viewpoint of the imaging tool; and displaying the changed image on the display system. The changed (Continued)

image includes a changed field of view corresponding to the detected movement of the user's head.

24 Claims, 10 Drawing Sheets

Related U.S. Application Data (60) Provisional application No. 62/487,833, filed on Apr. 20, 2017.

(51) Int. Cl.
| | |
|---|---|
| *A61B 90/00* | (2016.01) |
| *A61B 90/50* | (2016.01) |
| *G02B 27/00* | (2006.01) |
| *A61B 17/00* | (2006.01) |
| *A61B 34/00* | (2016.01) |
| *G02B 27/01* | (2006.01) |

(52) U.S. Cl.
CPC ............ *G02B 27/0093* (2013.01); *A61B 2017/00216* (2013.01); *A61B 2034/107* (2016.02); *A61B 34/25* (2016.02); *A61B 2090/365* (2016.02); *A61B 2090/502* (2016.02); *G02B 27/017* (2013.01)

(58) Field of Classification Search
CPC .... A61B 2017/00216; A61B 2034/107; A61B 2090/365; A61B 2090/502; A61B 2017/00707; A61B 34/30; A61B 34/00; A61B 90/00; G02B 27/0093; G02B 27/017

See application file for complete search history.

(56) References Cited

U.S. PATENT DOCUMENTS

| | | | |
|---|---|---|---|
| 11,589,937 B2* | 2/2023 | Lin | ............ A61B 34/35 |
| 2009/0036902 A1 | 2/2009 | DiMaio et al. | |
| 2011/0118748 A1 | 5/2011 | Itkowitz | |
| 2012/0154564 A1 | 6/2012 | Hoffman et al. | |
| 2013/0096575 A1 | 4/2013 | Olson et al. | |
| 2013/0249787 A1 | 9/2013 | Morimoto | |
| 2014/0018960 A1 | 1/2014 | Itkowitz | |
| 2014/0275760 A1 | 9/2014 | Lee et al. | |
| 2015/0046818 A1 | 2/2015 | Wade | |
| 2015/0148594 A1 | 5/2015 | Tadano et al. | |
| 2016/0089212 A1 | 3/2016 | Balicki et al. | |
| 2016/0191887 A1 | 6/2016 | Casas | |
| 2016/0331584 A1 | 11/2016 | Ren et al. | |
| 2017/0068081 A1 | 3/2017 | Hirayama | |
| 2017/0092002 A1 | 3/2017 | Mullins et al. | |
| 2017/0151034 A1 | 6/2017 | Oda et al. | |
| 2017/0232343 A1* | 8/2017 | Yoshioka | ............ H04N 7/185 463/31 |
| 2017/0255256 A1 | 9/2017 | Kim et al. | |
| 2017/0367771 A1* | 12/2017 | Tako | ............ G16H 20/40 |
| 2020/0038124 A1 | 2/2020 | Lin et al. | |
| 2020/0268462 A1 | 8/2020 | Popovic et al. | |

FOREIGN PATENT DOCUMENTS

| | | |
|---|---|---|
| EP | 3125737 A1 | 2/2017 |
| JP | H11104064 A | 4/1999 |
| JP | 2012223363 A | 11/2012 |
| WO | WO-9502233 A1 | 1/1995 |
| WO | WO-2015095715 A1 | 6/2015 |
| WO | WO-2016133644 A1 | 8/2016 |
| WO | WO-2016207628 A1 | 12/2016 |

OTHER PUBLICATIONS

Yip, Hiu Man, David Navarro-Alarcon, and Yun-hui Liu. "Development of an eye-gaze controlled interface for surgical manipulators using eye-tracking glasses." 2016 IEEE International Conference on Robotics and Biomimetics (ROBIO). IEEE, 2016 (Year: 2016).*

Extended European Search Report for Application No. EP18788291.5 mailed on Dec. 10, 2020, 09 pages.

International Preliminary Report on Patentability for Application No. PCT/US2018/028376, mailed on Oct. 31, 2019, 8 pages (ISRG10790/PCT).

International Search Report and Written Opinion for Application No. PCT/US2018/028376, mailed on Aug. 3, 2018, 11 pages (ISRG10790/PCT).

Office Action for Chinese Application No. CN20188023943, mailed Jul. 22, 2022, 17 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR CONSTRAINING A FIELD OF VIEW IN A VIRTUAL REALITY SURGICAL SYSTEM

CROSS-REFERENCE TO RELATED APPLICATIONS

This patent application is a continuation of U.S. application Ser. No. 16/496,153, filed Sep. 20, 2019, which is the U.S. national phase of International Application No. PCT/US2018/028376, filed Apr. 19, 2018, which designated the U.S. and claims priority to and the benefit of the filing date of U.S. Provisional Patent Application No. 62/487,833, filed Apr. 20, 2017, all of which are incorporated by reference herein in their entirety.

FIELD

The present disclosure is directed to systems and methods for performing a medical procedure or training for a medical procedure using a virtual reality display system and more particularly to systems and methods for providing constraints within a surgical system or surgical training system when using a virtual reality display system.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy. Some minimally invasive medical tools and imaging instruments may be teleoperated or otherwise computer-assisted. When performing teleoperational procedures or providing training simulations for teleoperational procedures, head-mounted display systems may be used to provide the clinician with an immersive augmented-reality or virtual reality experience. System controls are needed to provide for safe and reliable operation of teleoperational systems when using an immersive display system.

SUMMARY

The embodiments of the invention are summarized by the claims that follow below.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

In one embodiment a method of operating a surgical control system comprises displaying an image of a surgical environment, from a field of view of an imaging instrument, on a display system. The display system is configured for mounting to a head of a user. The method also includes detecting an imaging control input from the user and responsive to the detection of the imaging control input, enabling an imaging control mode of the surgical control system. The method also includes detecting a movement of the head of the user. While the surgical control system is in the imaging control mode and responsive to the user's head movement, an image of the surgical environment from a changed field of view of the imaging instrument is displayed. The changed field of view corresponds to the detected movement of the user's head.

In another embodiment, a method of operating a surgical control system comprises generating an image of a surgical environment from a viewpoint of an imaging tool having a field of view. A surgical instrument is positioned within the surgical environment. The method also includes displaying the image of a surgical environment on a display system. The display system is configured for mounting to a head of a user. The method also includes detecting a movement of the head of the user and determining if the movement of the user's head is within a boundary corresponding to the imaging tool field of view. If the movement of the user's head is within the boundary, the image of the surgical environment on the display system is changed by generating a changed viewpoint in the imaging tool field of view that corresponds with the detected movement of the user's head.

In another embodiment, a method of operating a surgical control system, the method comprises generating an image of a surgical environment. A surgical instrument is positioned within the surgical environment and is coupled to a manipulator arm having a range of motion. The method also includes displaying the image of a surgical environment on a display system. The display system is configured for mounting to a head of a user. The method also includes detecting a manipulator arm input motion from the user and determining if the manipulator arm input motion corresponds to movement of the manipulator arm within the range of motion. If the movement of the manipulator arm input motion corresponds to movement outside the range of motion of the manipulator arm, a ghost image of the surgical instrument is generated, wherein the ghost image moves in correspondence with the manipulator arm input motion.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Figure 1A:
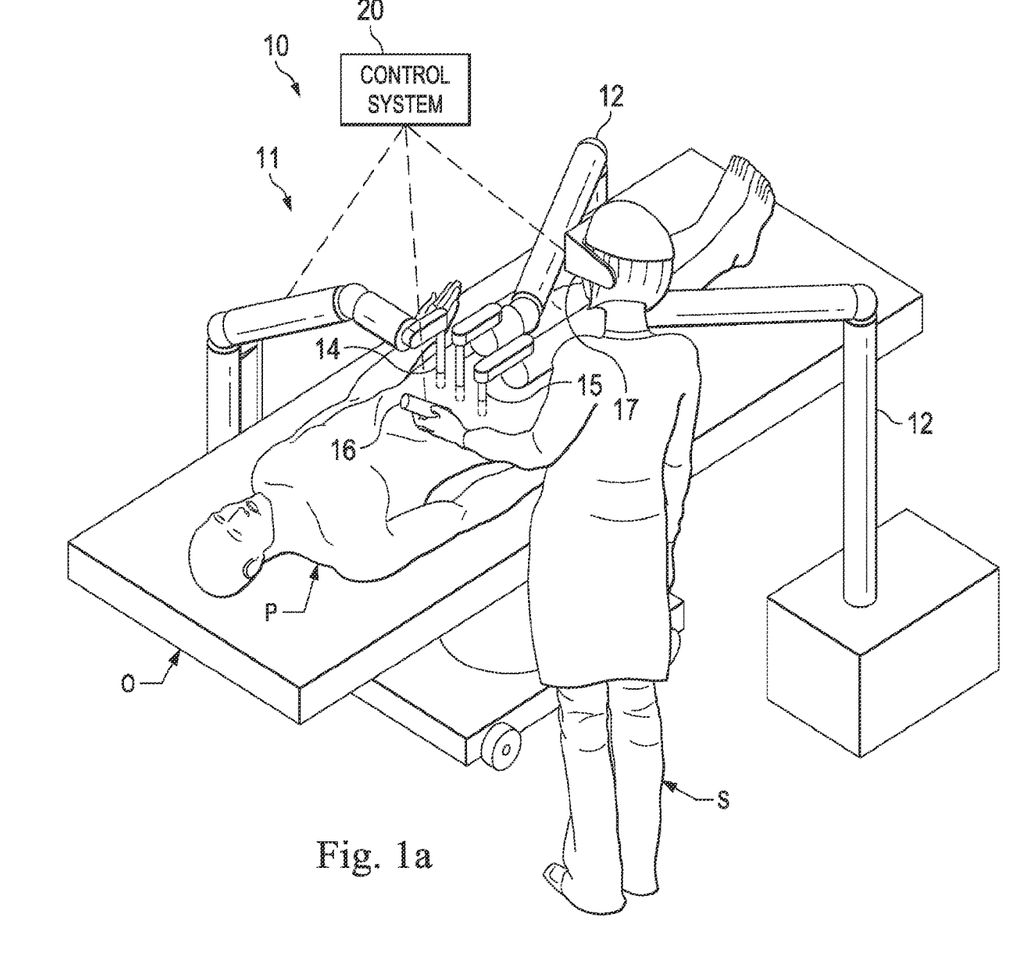
FIG. 1a provides a view of a surgical environment including a teleoperational surgical system including an immersive display system.

Referring to FIG. 1a of the drawings, a surgical environment 10 includes a teleoperational medical system 11 for use in, for example, medical procedures including diagnostic, therapeutic, or surgical procedures. The teleoperational medical system generally includes a teleoperational assembly mounted to or near an operating table O on which a patient P is positioned. The teleoperational assembly may include one or more modular manipulator arms 12. A medical instrument system 14 or an imaging system 15 may be operably coupled to a teleoperational manipulator (e.g. an arm) of the teleoperational assembly. The imaging system may be, for example, a stereoscopic endoscope imaging system. An operator input system 16 allows a surgeon S or other type of clinician to control the operation of the medical instrument system 14 and/or the imaging system 15. One or more assistant surgeons, anesthesiologists, or support personnel may also be present in the surgical environment.

Figure 2:
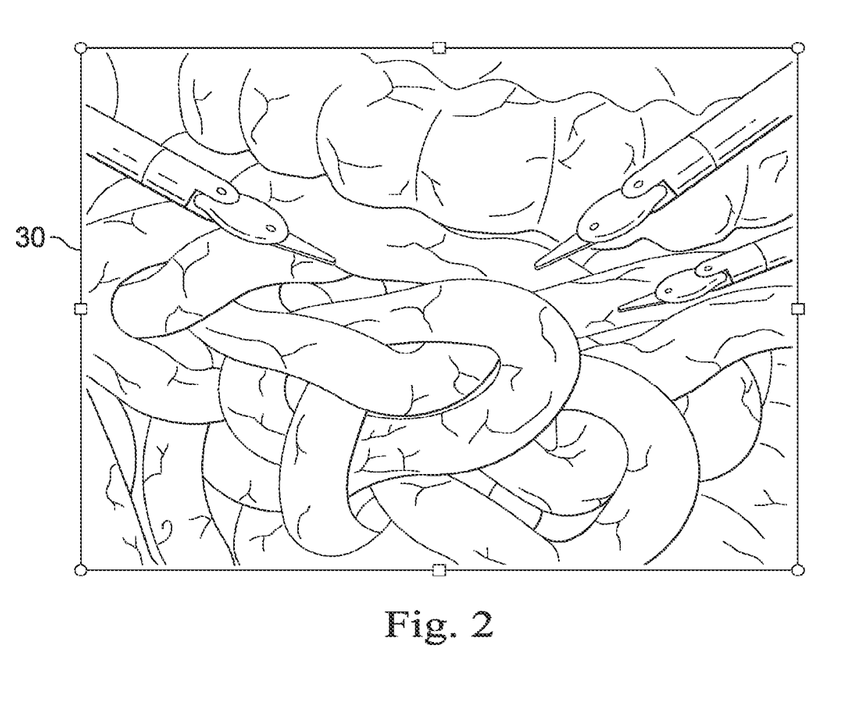
FIG. 2 provides a field of view image from an imaging instrument.

The teleoperational medical system also includes a display system 17 which may present images captured by the imaging system 15, surgical navigation and guidance images, and/or alphanumeric or symbolic information to assist the surgeon or assistants with the surgical procedure. The display system may be, for example, an immersive display system worn by the surgeon S. More specifically, the immersive display system may be a head-mounted display system for presenting an image of the interior anatomical environment from the imaging system 15, augmented or virtual images of the interior anatomical environment, images from external of the patient anatomy, interactive user interfaces, or other image-based, graphical, or textual information to the surgeon S. The head-mounted display system may be worn as a set of glasses or goggles covering both of a user's eyes. FIG. 2 illustrates a field of view image 30 from an imaging instrument 15 positioned within the interior anatomy of the patient P. The image 30 may be displayed on the display system 17. With stereoscopic image data, multiple viewpoints may be generated from the field of view stereoscopic image data while the imaging instrument is held in a static position. Thus, with an immersive display system, the field of view may be presented with slightly different viewpoint images as the user's head moves the display system. This may provide the user with a more immersive experience when viewing the field of view.

The teleoperational medical system also includes a control system 20 in communication with the operator input system 16, the teleoperational assembly and the display system 17, as described below.

Figure 3:
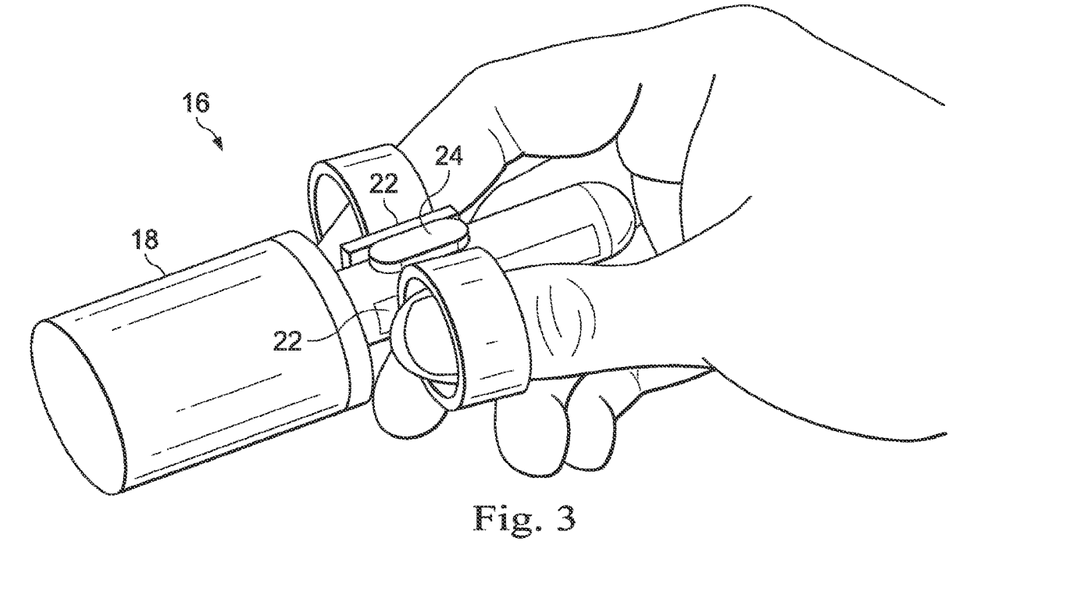
FIG. 3 illustrates a hand controller of a teleoperational surgical system.

In this embodiment, the operator input system 16 includes one or a set of operator hand controllers 18 (FIG. 3) for controlling one or multiple medical instrument systems 14 or the endoscopic imaging system 15. The input system also may include other types of user inputs including pedal inputs, gaze tracking, voice command recognition, head gesture recognition. In various alternatives the operator hand controllers 18 may be tethered by power and/or signal transmission cabling or may be untethered/wireless. As shown in FIG. 3, the operator controller 18 may include one or more of any number of a variety of input devices such as grip inputs 22 and trigger switch 24. The input devices may be used to, for example, move a distal end of an endoscopic imaging system within the patient P, close grasping jaw end effectors, apply an electrical potential to an electrode, deliver a medicinal treatment, or the like. In various alternatives, the operator input system may additionally or alternatively include joysticks, trackballs, data gloves, trigger-guns, hand or foot-operated controllers, voice recognition and control devices, touch screens, body motion or presence sensors, and the like. In some embodiments, the hand controller 18 will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the hand controller 18 may have more or fewer degrees of freedom than the associated medical instruments and still provide the surgeon with telepresence.

The manipulator arms 12 support and manipulate the medical instrument system 14 and/or the imaging system 15 while the surgeon S conducts the procedure from the patient side or another location within the surgical environment. The number of medical instrument systems 14 used at one time will generally depend on the diagnostic or surgical procedure and the space constraints within the operating room among other factors. Each arm 12 of the teleoperational assembly may include a kinematic structure of one or more servo or non-servo controlled links. The teleoperational arm 12 may also include a plurality of motors that drive inputs on the medical instrument system 14 or imaging system 15. These motors move in response to commands from the control system 20. The motors include drive systems which when coupled to the medical instrument system 14 or imaging system 15 may move the systems into or out of a naturally or surgically created anatomical orifice. Other motorized drive systems may move the distal end of the systems in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The control system 20 includes at least one memory and at least one processor, and typically a plurality of processors, for effecting control between the medical instrument system, the imaging system 15, the operator input system 16, the display system 17, and other auxiliary systems which may include, for example, additional imaging systems, audio systems, fluid delivery systems, display systems, illumination systems, steering control systems, irrigation systems, and/or suction systems. The control system 28 also includes programmed instructions (e.g., a computer-readable medium storing the instructions) to implement some or all of the methods described in accordance with aspects disclosed herein. While control system 20 is shown as a single block in the simplified schematic of FIG. 1a, the system may include two or more data processing circuits with one portion of the processing optionally being performed on or adjacent the teleoperational assembly, another portion of the processing being performed at the operator input system 16, and the like. The control system 20 may employ any of a wide variety of centralized or distributed data processing architectures. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system or the imaging system. Responsive to the feedback, the servo controllers transmit signals to the operator input system 16. The servo controller(s) may also transmit signals instructing teleoperational assembly to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly. In some embodiments, the servo controller and teleoperational assembly are provided as part of a teleoperational arm positioned adjacent to the patient's body.

The control system 20 can be communicatively coupled with the imaging system 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

Figure 1B:
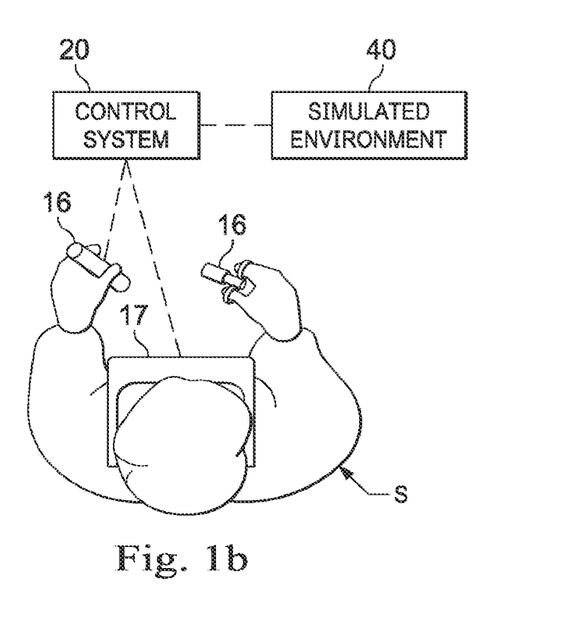
FIG. 1B provides a view of a simulated surgical environment including a teleoperational surgical system including an immersive display system.

As shown in FIG. 1B, the control system 20, operator input system 16 and immersive display system 17 may also be used to conduct a procedure with a simulated surgical environment 40. The simulated surgical environment 40 may be viewed on the immersive display system 17 by the user S. In one embodiment, the simulated surgical environment is a three dimensional, virtual-reality environment representing a surgical environment that may be used for designing and providing clinician training. The field of view of a simulated imaging system may appear similar to a live field of view image 30. The simulated surgical environment may be a pre-recorded image of a patient anatomical environment, a computer-generated illustration of a patient anatomical environment, or a hybrid of the two. In the simulator environment, virtual instruments in the field of view image may be operated using the hand controllers 18. Likewise, the hand controllers may be used to adjust the simulated field of view by moving a simulation imaging system (e.g. a virtual endoscope). In various embodiments, the simulated surgical environment may be a complete virtual reality environment in which movements of the user S, such as head movements or inputs to the input system 16, are tied to parameters of virtual components (e.g., virtual instruments, a virtual imaging system) in the virtual reality environment. In these entirely virtual simulated environments, user movements are not tied to physical components in a physical surgical environment. In some embodiments, user inputs may be provided by tracked gaze or head motion, without the use of hand controllers.

In alternative embodiments, the simulated surgical environment may be a physical, artificial surgical environment designed to mimic a natural anatomy or to provide specialized procedure training. In these alternative embodiments, user inputs may be tied to physical components active in the artificial environment. In still other alternative embodiments, the simulated surgical environment may be a hybrid environment including both virtual reality elements and physical components.

The immersive display systems allow a user to experience a live or simulated surgical environment as if the user were present within the environment. A head mounted immersive display system physically allows a user to have full range of translational and rotational motion that may not correspond to the physical constraints imposed by the kinematics and safety features of the teleoperational system. The systems and methods described below may be implemented to impose constraints on or augment the user's experience when using an immersive display system in a live or simulated surgical environment.

In a traditional teleoperational surgical system in which a user is positioned at a stationary operator console, the system enters an engagement mode (also known as a "head-in" mode) when sensors detect that the user's head is positioned in a viewfinder and the user is able to visualize the surgical environment displayed in the viewfinder via images captured by the imaging system. The "following mode" of a teleoperational medical system is a system operational state in which the movement of the operator input system, such as the hand controllers, effects movement of the instruments positioned in the patient anatomy. Generally, before the teleoperational medical system can enter the following mode for performing a surgical procedure, the system must first be in the engagement mode. To safely perform a teleoperational procedure with a traditional system, movement of the instruments within the patient anatomy may be suspended when the operator looks away or otherwise exits the engagement mode, indicating that the display system is not visible to the operator.

Figure 4:
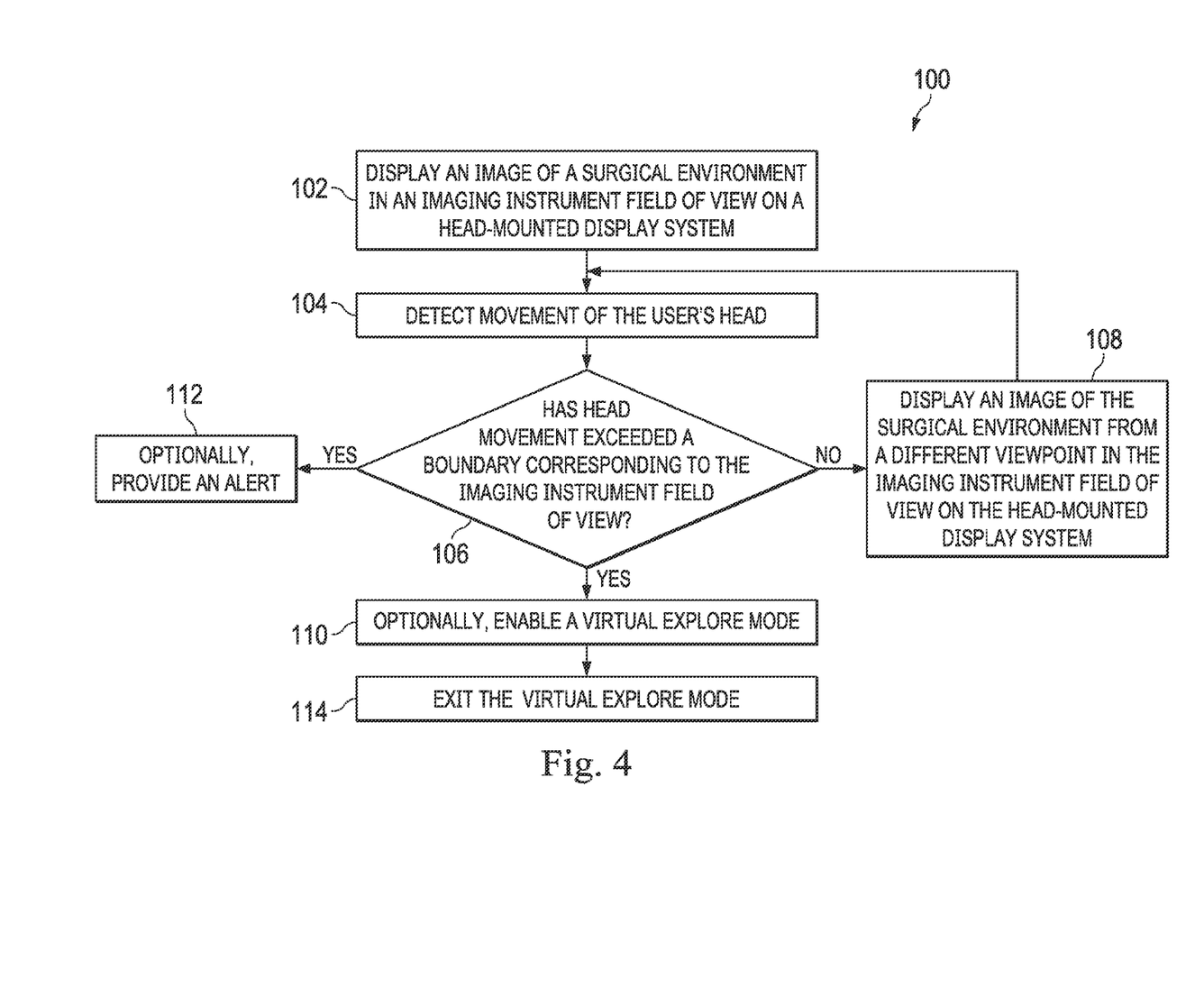
FIG. 4 is a flowchart providing a method for entering and exiting a virtual explore mode of the teleoperational surgical system.

When the display system is not in a fixed position within an operator console, as is the case with an operator-mounted immersive display system, the teleoperational system may be constrained or augmented to provide a virtual engagement mode that indicates the operator is able to visualize the surgical environment in the immersive display prior to entering an instrument following mode. FIG. 4 is a flowchart providing a method 100 for entering and exiting virtual engagement and virtual explore modes of a teleoperational surgical system. The teleoperational surgical system may be, for example a teleoperational surgical system 11 for use in a live surgical environment 10 or a simulator environment 40. The method 100 is illustrated in FIG. 4 as a set of operations or processes 102 through 114. Not all of the illustrated processes 102 through 114 may be performed in all embodiments of method 100. Additionally, one or more processes that are not expressly illustrated in FIG. 4 may be included before, after, in between, or as part of the processes 102 through 114. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

Figure 5:
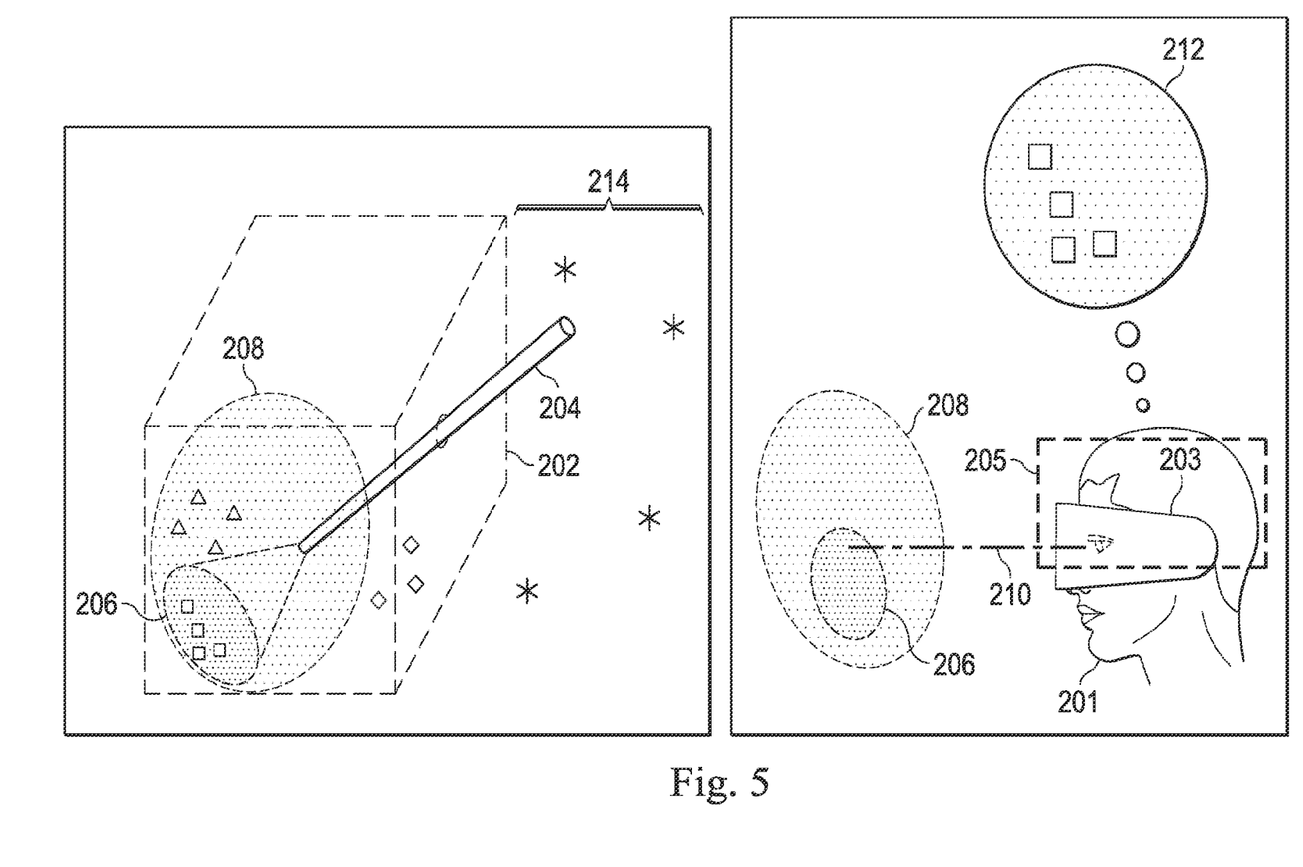
FIGS. 5-8 illustrate a surgical environment, an external environment, and displayed images on an immersive display system.

At a process 102, an image of a surgical environment visible in the field of view of an imaging instrument is displayed. The image is displayed on a user-mounted immersive display system. With reference to FIG. 5, a surgical environment 202 (e.g., an interior anatomy of a live patient or a simulated surgical environment) may be visible with an imaging instrument 204 having a current field of view 206 and a potential field of view 208. The potential field of view may be defined by the range of motion of the imaging instrument 204. An environment 214 is external to the surgical environment 202. A user 201 (e.g., a surgeon S) wearing a head-mounted immersive display system 203 (e.g., display system 17) has a view direction 210 toward the current field of view 206. A visible image 212 is presented on the display system 203. In this position the user may be in a virtual engaged mode. In the virtual engaged mode, the user visualizes the current field of view. From the virtual engaged mode, the instrument following mode may be entered in which instruments in the field of view may be moved under control of the operator input system.

At a process 104, movement of the user's head is detected. At a process 106, a determination is made as to whether the user's head (or a portion of the head such as the eyes) is within a boundary that corresponds to and allows the user to view the field of view. The position and view direction of the user's head may be evaluated to determine whether the current field of view is visible to the user.

Figure 6:
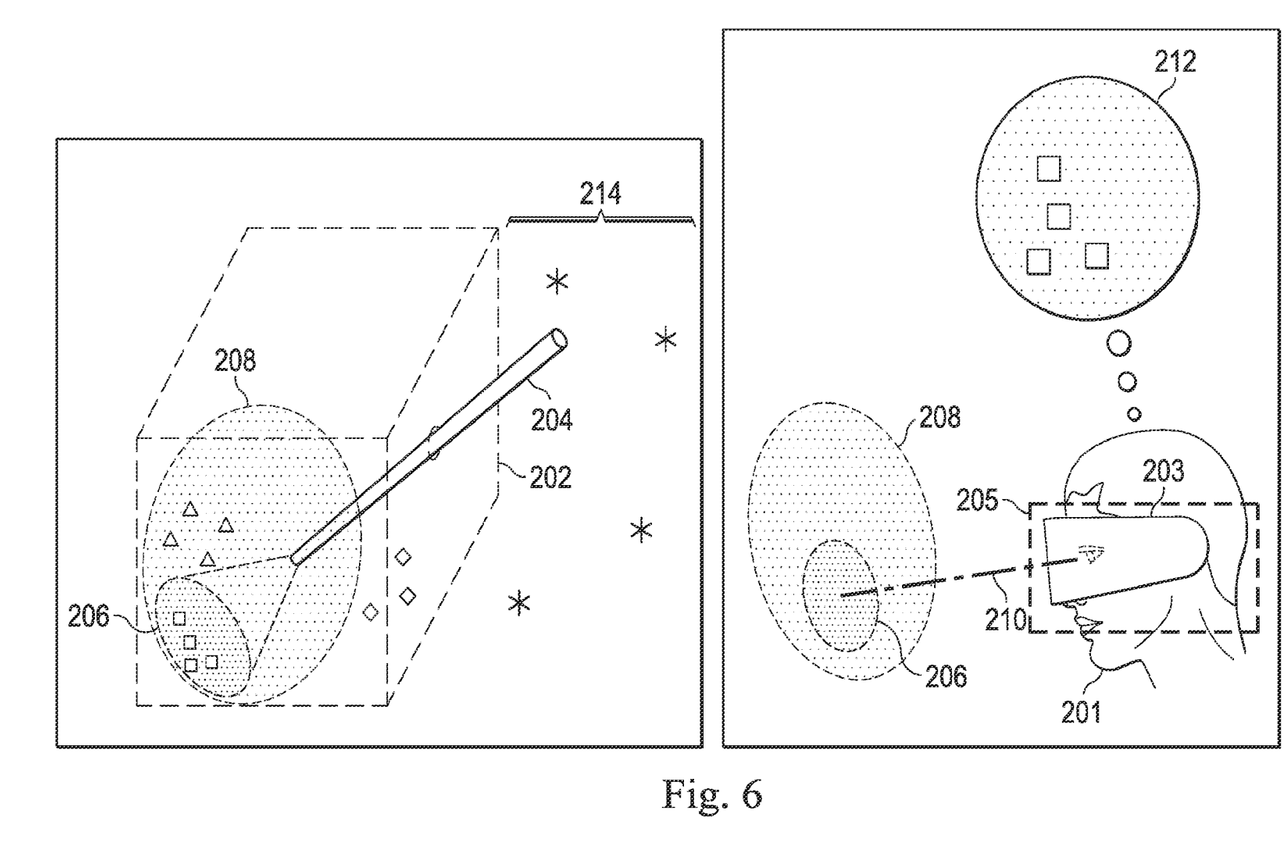

At a process 108, if the head movement has not exceeded the boundary and/or the user's head remains directed toward the current field of view, the image on the display system is still an image of the field of view 206. If the image data is three dimensional, for example from a stereoscopic endoscope instrument, the image of the field of view may be presented from a slightly different viewpoint corresponding to the detected movement of the user's head. As shown in FIG. 6, the head of the user 201 has moved, but the user's eye view direction 210 is directed toward the current field of view 206 and the user's head and eyes are within a boundary 205 corresponding to the field of view 206. Thus the visible image 212 is an image of the field of view 206 from a slightly shifted viewpoint corresponding to the movement of the user's head.

At a process 110, if the head movement has exceeded the boundary and/or the user's head is not directed toward the current field of view, the image on the display system changes to notify the user that the field of view is not visible on the display system. For example, at an optional process 110, the teleoperational system may enter a virtual explore mode. In another example at an optional process 112, the teleoperational system may provide an alert. In the example embodiments of FIGS. 7 and 8, movement of the user's head is such that the user's eyes are now outside of the boundary 205 and the view direction 210 is no longer directed toward the current field of view 206. Optionally, a message 212b may be displayed on the display system 203 to alert the user that he has moved outside the current field of view. The message may include text, graphics, or other images to alert the user or direct the user's head back toward the field of view. The teleoperational system may suspend following mode such that movement of the hand controllers do not move the surgical instruments in the surgical environment.

Figure 7:
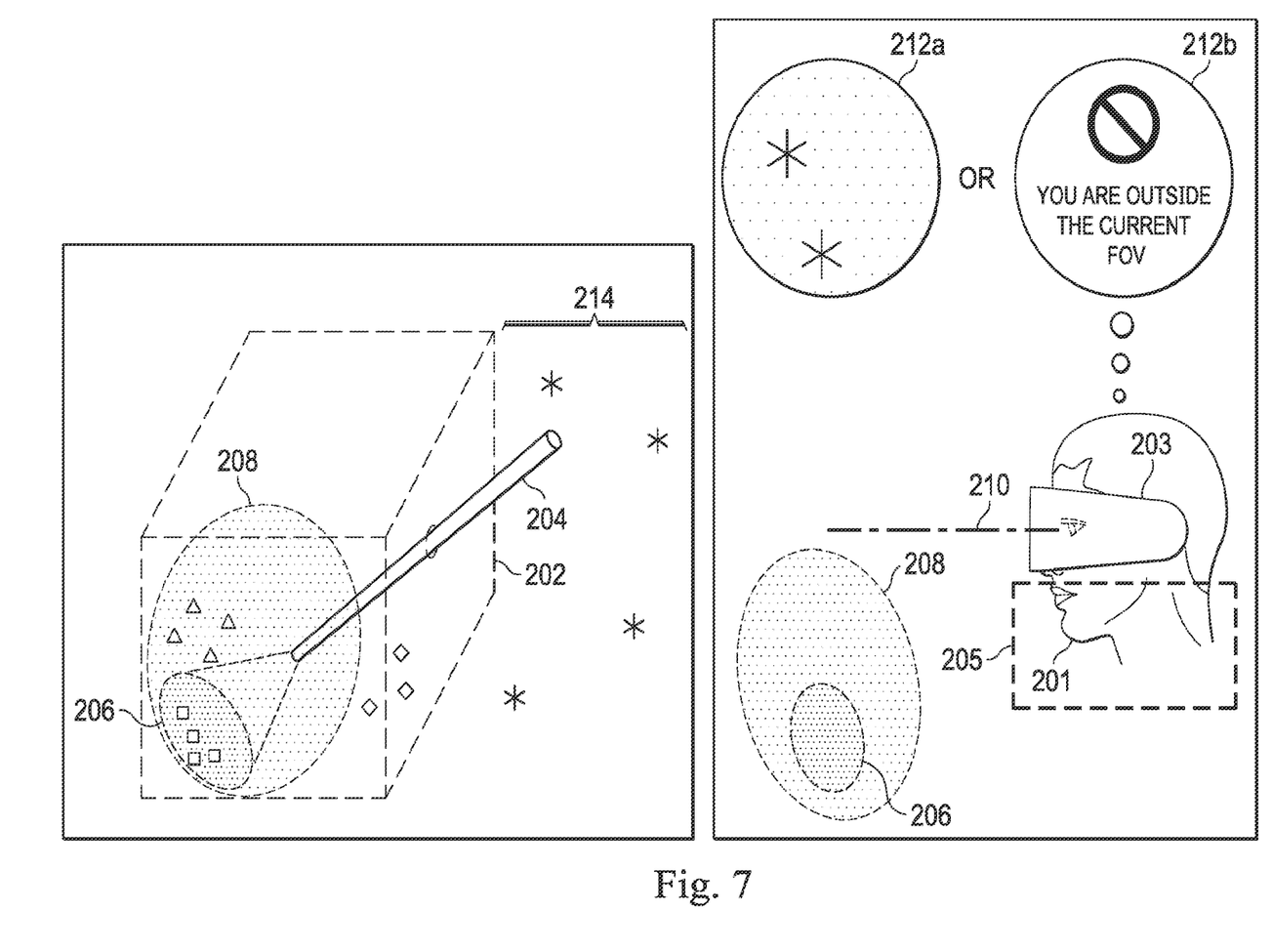
Figure 8:
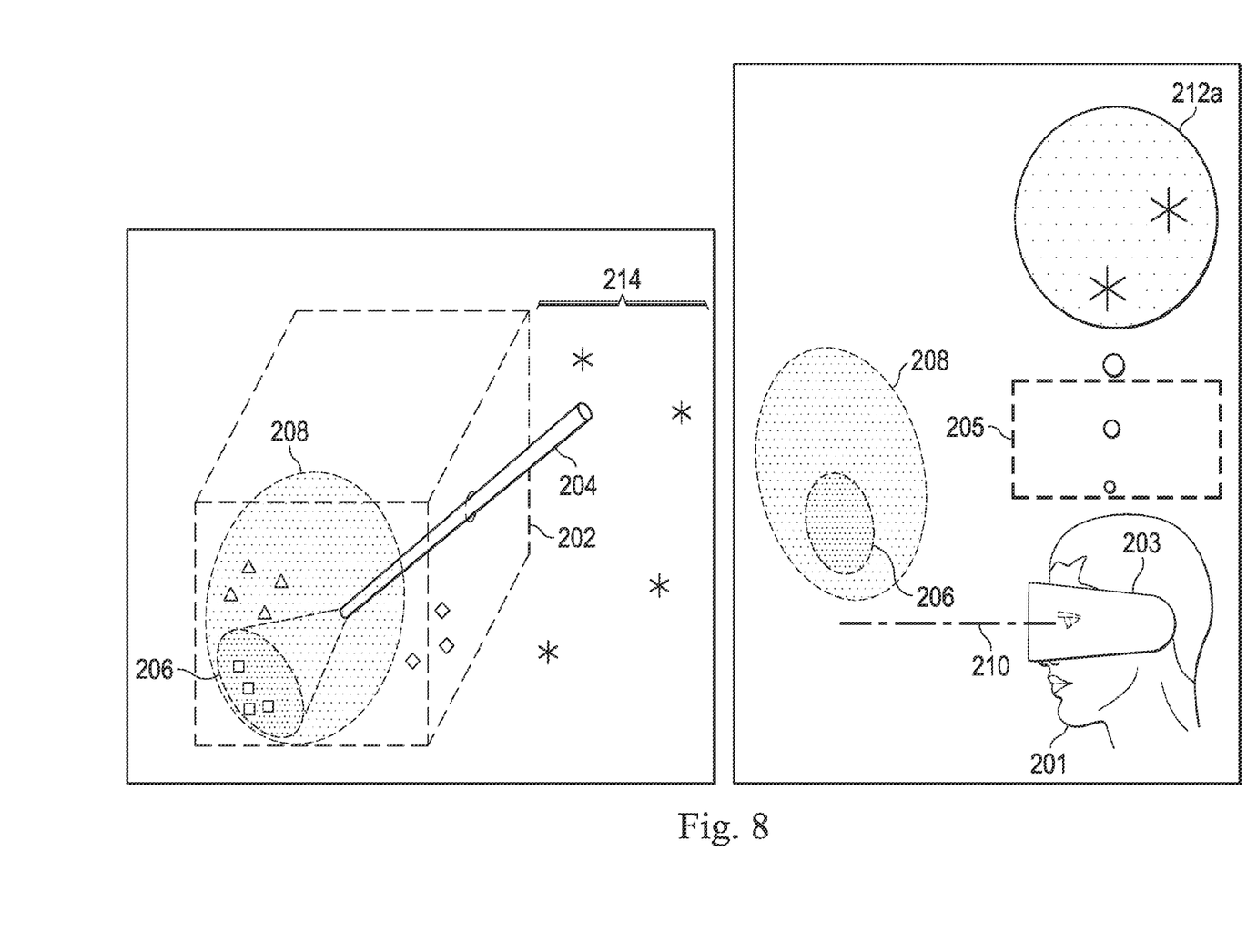

Optionally, the teleoperational system may enter a virtual explore mode in which image 212a on the display system is a virtual user interface that may include images of an environment 214 outside the surgical environment such as an external environment surrounding the patient or another remote viewpoint, separated from the viewpoint of the imaging instrument. Alternatively the virtual user interface may allow the use to access, for example, an interactive control menu for controlling features of the teleoperational system, status information about the patient or components of the teleoperational system, or a see-through image of the environment in front of his head.

At a process 114, directions may be provided to lead the user to move his eyes back within the boundary so that the field of view 206 is again visible. Directions may be, for example, in the form of an audio recording providing verbal instructions for head movement, a sound that changes as the movement of the head changes, a set of textual instructions, a graphical movement map, a visual homing beacon, or a scene of the field of view that changes color or focus as the direction of view moves toward the field of view. When the user's head matches the last field of view direction, teleoperational system may exit virtual explore mode and return to following or engagement mode. An audio, visual, or tactical indication may alert the user that virtual explore mode has been exited.

Alternatively the user may exit the virtual explore mode and re-enter an engagement mode, a following mode, or an imaging control mode at a newly calibrated head position. The user may provide an indication that the user is working from a new position or the system may receive an indication that a large translational movement (exceeding a threshold movement value and indicating that the user is working from a new position) has been detected. Based on the indication, the system may establish a new position, orientation, and set of head boundaries for the user's new location. From this new location, the position and view direction of the user's head may be evaluated to determine the user's current field of view. For example, if a user begins by standing on one side of a patient and then moves to the opposite side of the table, the system will initially enter the virtual explore mode as the user's head moves beyond the boundary. The system may exit the virtual explore mode and re-enter a mode, such as following or imaging control mode, on the opposite side of the table. With the new head position and orientation detected, the imaging system view displayed to the user is based on the user's new position and orientation.

Figure 9:
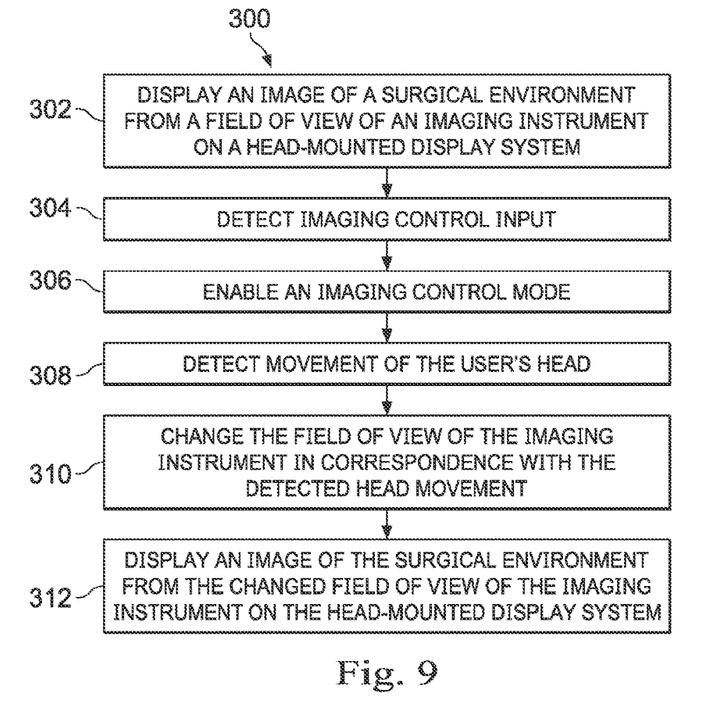
FIG. 9 is a flowchart providing a method for operating within an imaging control mode of the teleoperational surgical system.

The teleoperational system may be constrained to provide a virtual imaging control mode that requires the user input prior to moving the actual or simulated imaging instrument within the surgical environment. FIG. 9 is a flowchart 300 providing a method for entering and operating within a virtual imaging control mode of a teleoperational surgical system. The teleoperational surgical system may be, for example a teleoperational surgical system 11 for use in a live surgical environment 10 or a simulator environment 40. The method 300 is illustrated in FIG. 9 as a set of operations or processes 302 through 312. Not all of the illustrated processes 302 through 312 may be performed in all embodiments of method 300. Additionally, one or more processes that are not expressly illustrated in FIG. 9 may be included before, after, in between, or as part of the processes 302 through 312. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

Figure 10:
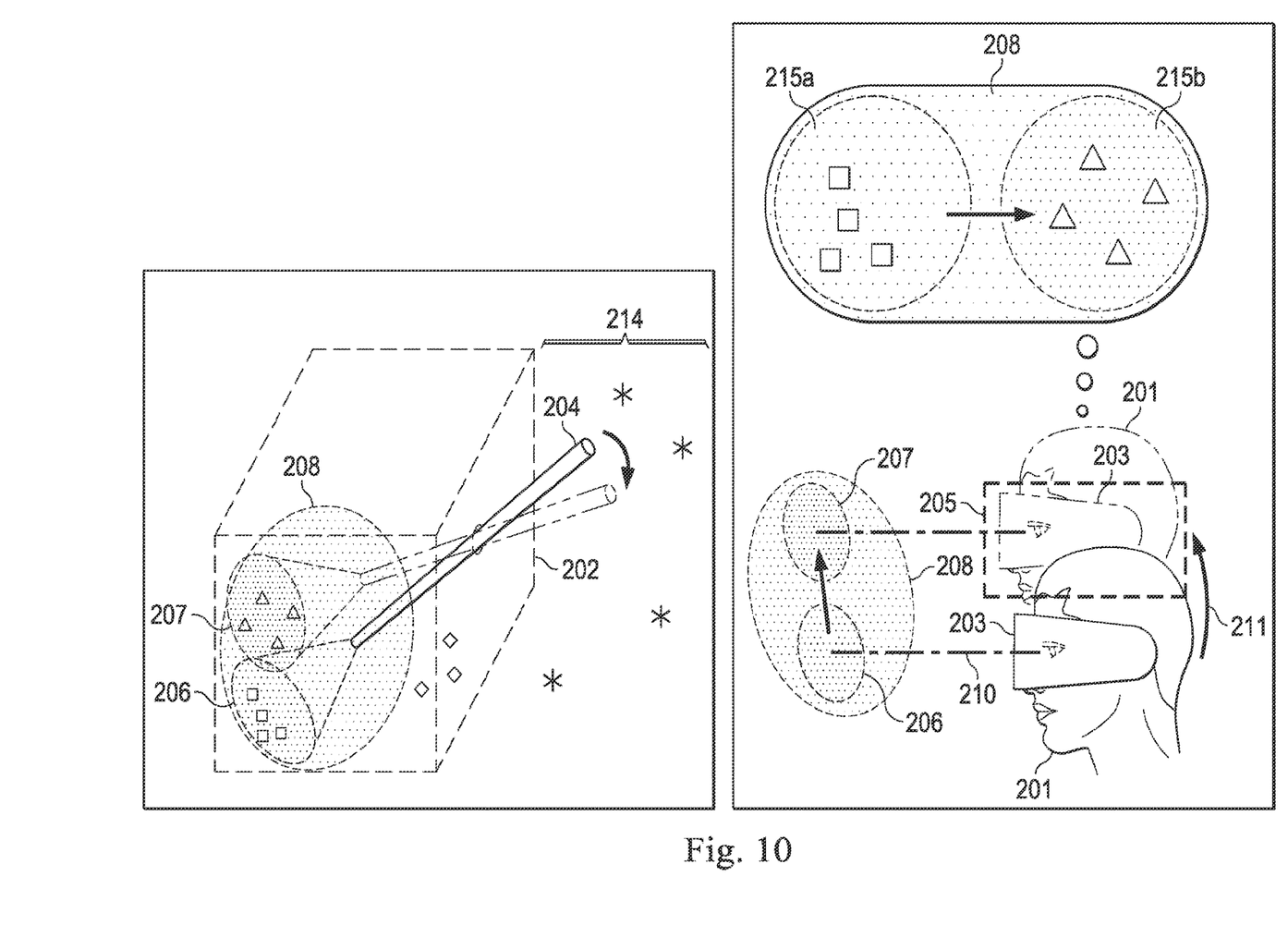
FIG. 10 illustrates a surgical environment, an external environment, and displayed images on an immersive display system.

At a process 302, an image of a surgical environment visible in the field of view of an imaging instrument is displayed. The image is displayed on a user-mounted immersive display system. With reference to FIG. 10, a user 201 may want to change the current field of view 206 within the potential field of view 208 defined by the range of motion of the imaging system 204.

At a process 304, an imaging control input is detected. The imaging control input may be a clutching input that transitions the teleoperational system out of an engagement or following mode. For example, the image control input may be an input at a hand controller 18 such as pushing a button 24. Other types of user inputs including switches, hand gestures, pedal movements or other type of deliberate user input may be a suitable image control input for initiating an image control mode.

At a process 306, responsive to the detection of the imaging control input, the teleoperational system enters an imaging control mode. In the imaging control mode, the field of view of the imaging instrument may be changed by moving the imaging instrument within the instrument's range of motion. In the imaging control mode, the surgical instruments are locked in place and movement of the operator input system does not cause a corresponding motion of the surgical instruments. In the imaging control mode, the imaging instrument may be moved in response to a user motion such as movement of the user's head or movement of operator input system.

At a process 308, movement of the user's head is detected. Alternatively another type of user input such as movement of a hand controller 18 may be detected. For example, with reference to FIG. 10, a movement 211 of the head 201 may be detected. The view direction 210 changes with the movement of the user's head.

At a process 310, the field of view of the imaging instrument changes from field of view 206 to field of view 207. Field of view 207 is the field of view of the imaging system 204 after it has been moved in correspondence with the detected head movement 211.

At a process 312, an image of the surgical environment from the changed field of view is displayed on the display system. For example, with reference to FIG. 10, the image 215a of the field of view 206 on the display system 203 is changed to an image 215b of field of view 207.

When the teleoperational system is in the imaging control mode, movement of the hand controllers 18 may cause movement of the instrument 204 within the range of motion and may consequently change the field of view of the instrument 204. Alternatively, movement of the hand controllers 18 may cause ghosted images of the surgical instruments in the field of view to move in accordance with the movement of the controllers.

If the detected motion of the user's head does not correspond to a movement within the range of motion of the imaging instrument, the teleoperational system may enter the virtual explore mode and provide images of other environments, user interfaces, or information and previously described. The virtual explore mode may be exited by matching the user's head with the last position and orientation of the imaging system, as previously described.

The imaging control mode may be exited when an additional imaging control input (e.g., depressing a button on the controller 18) is detected. In various alternative embodiments, the imaging control mode may require continuous activation of the imaging control input (e.g., continuous depression of a button on the controller 18) such that discontinuing the control input transitions the teleoperational system from imaging control mode into an engagement or following mode.

Figure 11:
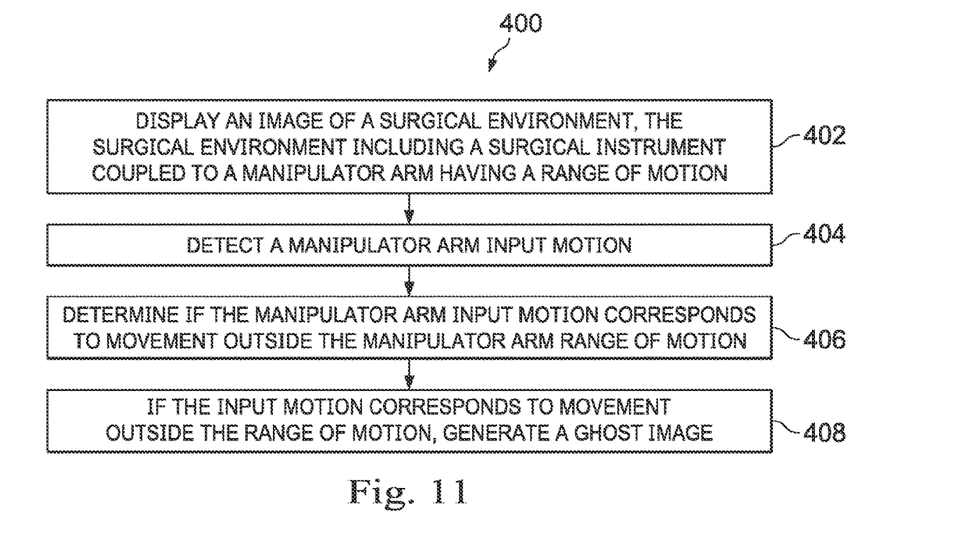
FIG. 11 illustrates a method for entering and operating within a virtual manipulator arm mode of a teleoperational system.

The teleoperational system may be constrained to provide a virtual manipulator arm mode that indicates when a user's arm motion is outside of a range of motion that corresponds to an allowable range of motion of the manipulator arm (e.g., arm 12). FIG. 11 is a flowchart 400 providing a method for entering and operating within a virtual manipulator arm mode of a teleoperational system. The teleoperational surgical system may be, for example a teleoperational surgical system 11 for use in a live surgical environment 10 or a simulator environment 40. The method 400 is illustrated in FIG. 11 as a set of operations or processes 402 through 408. Not all of the illustrated processes 402 through 408 may be performed in all embodiments of method 400. Additionally, one or more processes that are not expressly illustrated in FIG. 11 may be included before, after, in between, or as part of the processes 402 through 408. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

At a process 402, an image of a surgical environment is displayed. The image is displayed on a user-mounted immersive display system. The surgical environment image may include an images of a surgical instrument and/or portions of a manipulator arm to which the instrument is coupled.

At a process 404, a manipulator arm input motion is detected. For example movement of a user's arm or hand may be detected as a manipulator arm input motion. At a process 406, the teleoperational system determines if the manipulator arm input motion corresponds to movement outside of the physical manipulator arm (e.g. arm 12) range of motion. If the input motion corresponds to movement of the manipulator am outside of the range of motion, the teleoperational system enters a virtual manipulator arm mode. In the virtual manipulator arm mode, movement of the user's arm does not cause corresponding motion of the physical manipulator arm and a ghost image of the surgical instrument or a ghost image of the manipulator arm is shown moving on the display system with motion corresponding to the manipulator arm input motion. To exit the virtual manipulator arm mode, the user may be directed back to the last allowable position of the surgical instrument or manipulator arm. The directions back to the matched position may be similar to those provided to the user to exit the virtual explore mode as previously described.

While certain exemplary embodiments of the invention have been described and shown in the accompanying drawings, it is to be understood that such embodiments are merely illustrative of and not restrictive on the broad invention. Additionally, it is to be understood that the embodiments of the invention are not limited to the specific constructions and arrangements shown and described, since various other modifications may occur to those ordinarily skilled in the art.

Further, in the detailed description of the embodiments of the invention, numerous specific details have been set forth in order to provide a thorough understanding of the disclosed embodiments. However, it will be obvious to one skilled in the art that the embodiments of this disclosure may be practiced without these specific details. In some instances, well known methods, procedures, and components have not been described in detail so as not to unnecessarily obscure aspects of the embodiments of the invention.

What is claimed is:

1. A method of operating a surgical control system, the method comprising:
generating an image of a surgical environment from a viewpoint of an imaging tool, the image including a field of view;
displaying the image of the surgical environment on a display system, the display system configured to be mounted to a head of a user;
detecting a movement of the head of the user;
determining if the movement of the user's head is within a boundary corresponding to the field of view; and
if the movement of the user's head is determined to be within the boundary:
generating a changed image of the surgical environment from a changed viewpoint of the imaging tool, the changed image including a changed field of view corresponding to the detected movement of the user's head; and
displaying the changed image of the surgical environment on the display system.

2. The method of claim 1 further comprising:
if the movement of the user's head exceeds the boundary, locking the image of the surgical environment.

3. The method of claim 1 further comprising:
if the movement of the user's head exceeds the boundary, enabling a virtual explore mode of the surgical control system.

4. The method of claim 3 further comprising:
while the surgical control system is in the virtual explore mode and responsive to the user's head movement, displaying an image of the surgical environment on the display system from a remote viewpoint separated from the viewpoint of the imaging tool.

5. The method of claim 3 further comprising:
while the surgical control system is in the virtual explore mode and responsive to the user's head movement, displaying an interactive virtual user interface.

6. The method of claim 3 further comprising:
providing directions for exiting the virtual explore mode, wherein the directions guide a head movement of the user to a direction that matches the viewpoint of the imaging tool.

7. The method of claim 6 wherein the directions include audible directions.

8. The method of claim 6 wherein the directions include visual images presented on the display system.

9. The method of claim 6 further comprising providing an indication to the user that the surgical control system has exited the virtual explore mode.

10. The method of claim 3 further comprising:
while the surgical control system is in the virtual explore mode and responsive to the user's head movement, displaying an image of an environment external of a patient anatomy.

11. The method of claim 3 further comprising:
providing directions for exiting the virtual explore mode; and
when the surgical control system exits the virtual explore mode, entering an imaging control mode.

12. The method of claim 3 further comprising:
providing directions for exiting the virtual explore mode; and
when the surgical control system exits the virtual explore mode, entering an engagement mode.

13. The method of claim 3 further comprising:
providing directions for exiting the virtual explore mode; and
when the surgical control system exits the virtual explore mode, entering a following mode, wherein in the following mode, a medical instrument of the surgical control system is configured to move in response to movement of a user input device of the surgical control system.

14. The method of claim 3 further comprising:
providing directions for exiting the virtual explore mode; and
when the surgical control system exits the virtual explore mode, receiving a user input indicating that a direction of the head of the user matches a second changed viewpoint of the imaging tool.

15. The method of claim 1 wherein the surgical environment is a simulated surgical environment and the image is from a virtual imaging tool having a virtual range of motion.

16. A medical system comprising:
a display configured to be mounted to a head of a user;
an imaging device; and
a control system, the control system configured to:
generate an image of a surgical environment from a viewpoint of the imaging device, the image including a field of view;
display the image of the surgical environment on the display;
detect a movement of the head of the user;
determine if the movement of the user's head is within a boundary corresponding to the field of view; and
if the movement of the user's head is determined to be within the boundary:
generate a changed image of the surgical environment from a changed viewpoint of the imaging device, the changed image including a changed field of view corresponding to the detected movement of the user's head; and
display the changed image of the surgical environment on the display.

17. The medical system of claim 16, wherein the control system is further configured to enable a virtual explore mode of the medical system if the movement of the user's head exceeds the boundary.

18. The medical system of claim 17, wherein the control system is further configured to, while the medical system is in the virtual explore mode and responsive to the user's head movement, display an image of the surgical environment on the display from a remote viewpoint separated from the viewpoint of the imaging device.

19. The medical system of claim 17, wherein the control system is further configured to, while the medical system is in the virtual explore mode and responsive to the user's head movement, display an interactive virtual user interface.

20. The medical system of claim 17, wherein the control system is further configured to provide directions for exiting the virtual explore mode, wherein the directions guide a head movement of the user to a direction that matches the viewpoint of the imaging device.

21. The medical system of claim 20, wherein the control system is further configured to provide an indication to the user that the medical system has exited the virtual explore mode.

22. The medical system of claim 17, wherein the control system is further configured to, while the medical system is in the virtual explore mode and responsive to the user's head movement, display an image of an environment external of a patient anatomy.

23. The medical system of claim 17, wherein the control system is further configured to:
provide directions for exiting the virtual explore mode; and
when the medical system exits the virtual explore mode, enter an imaging control mode, an engagement mode, or a following mode.

24. The medical system of claim 17, wherein the control system is further configured to:
provide directions for exiting the virtual explore mode; and
when the medical system exits the virtual explore mode, receive a user input indicating that a direction of the head of the user matches a second changed viewpoint of the imaging device.

* * * * *